United States Patent [19]

Oi et al.

[11] Patent Number: 5,196,590
[45] Date of Patent: Mar. 23, 1993

[54] METHOD OF MAKING 2,4,5-TRIHALOBENZOIC ACID

[75] Inventors: J.Steven Oi, Amherst; Joseph J. Moritz, Grand Island, both of N.Y.

[73] Assignee: Occidental Chemical Corporation, Niagara Falls, N.Y.

[21] Appl. No.: 881,112

[22] Filed: May 11, 1992

[51] Int. Cl.$^5$ .............................................. C07C 63/04
[52] U.S. Cl. ..................................................... 562/493
[58] Field of Search ........................................ 562/493

[56] References Cited

U.S. PATENT DOCUMENTS

| 2,439,237 | 4/1968 | Cass et al. | 562/480 |
| 4,769,492 | 9/1988 | Kaieda et al. | 562/479 |
| 4,769,493 | 9/1988 | Ito et al. | 562/480 |
| 4,935,541 | 6/1090 | O'Reilly | 562/479 |

FOREIGN PATENT DOCUMENTS

| 0194671 | 9/1986 | European Pat. Off. . |
| 3810093 | 5/1989 | Fed. Rep. of Germany . |
| 62-111942 | 5/1987 | Japan . |
| 64-52737 | 2/1989 | Japan . |
| 2-145538 | 6/1990 | Japan . |

Primary Examiner—Paul J. Killos
Attorney, Agent, or Firm—Wayne A. Jones; Richard D. Fuerle

[57] ABSTRACT

Disclosed is a method of making 2,4,5-trihalobenzoic acid by heating to a temperature of about 130° to about 190° C. a composition that comprises water, a mineral acid, and a compound having the general formula

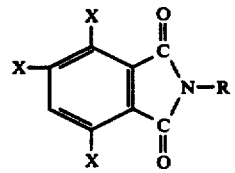

where "X" is fluorine, chlorine, or bromine and "R" is alkyl from $C_1$ to $C_{10}$ or aryl. The fluorine product is useful in making quinolone antibacterial drugs.

20 Claims, No Drawings

METHOD OF MAKING 2,4,5-TRIHALOBENZOIC ACID

BACKGROUND OF THE INVENTION

This invention relates to a method of making 2,4,5-trihalobenzoic acid from 2,4,5-trihalo-N-alkyl or aryl phthalimide. In particular, it relates to a method in which 3,4,6-trihalo-N-alkyl or aryl phthalimide is heated to a temperature of about 130° to about 190° C. in the presence of water and a mineral acid to produce 2,4,5-trihalobenzoic acid in a high yield.

2,4,5-trifluorobenzoic acid, a useful intermediate for manufacturing quinolone antibacterial drugs, can be prepared by selective decarboxylation of trifluorophthalic acid. However, preparation of trifluorophthalic acid from inexpensive trichlorophthalic or tetrachlorophthalic anhydride, via by direct fluorination using KF treatment is difficult because of breakage of carboxylic groups under the harsh fluorination conditions.

SUMMARY OF THE INVENTION

We have discovered a method of producing 2,4,5-trihalobenzoic acid from 3,4,6-trihalo-N-alkyl or aryl phthalimide by heating it with water and a mineral acid. We have found that although heating with water alone will decarboxylate the phthalimide and produce the corresponding benzoic acid, it also produces about 20 to about 50% of undesirable by-product, and that only by adding sufficient mineral acid can the production of the undesirable by-products be reduced to below 5%.

Production of trifluorobenzoic acid by our method is simple and inexpensive, but highly selective. Because the phthalimide group is symmetrical, one would not expect to form a predominant quantity of 2,4,5-trihalobenzoic acid over 2,3,5-trihalobenzoic acid. But very surprisingly, we have discovered that about 95% of the product is the desirable 2,4,5 isomer and only 5% of the product is the 2,3,5 isomer.

DESCRIPTION OF THE INVENTION

The starting material for the process of this invention is a phthalimide having the general formula

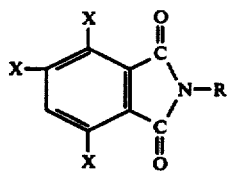

Each "X" can be independently selected from fluorine, chlorine, or bromine but preferably each "X" is the same halogen as those compounds are easier to obtain. The "R" in the formula is alkyl from $C_1$ to $C_{10}$ or aryl. Preferably, "X" is fluorine since the fluorinated compounds are a more useful intermediate for making quinolone antibacterials, and preferably "R" is methyl because that compound is more readily available from fluorination.

The 3,4,6-trifluoro-N-R-phthalimide starting material can be made by at least two processes. In the first process, inexpensive tetrachlorophthalic anhydride is imidized to prepare the N-substituted phthalimide with $RNH_2$ in sulfolane to protect the carboxylic groups from the harsh conditions of fluorination. The phthalimide compound is then fluorinated, for example with potassium fluoride in sulfolane, to produce the corresponding tetrafluoro N-R phthalimide. Finally, the tetrafluoro N-R phthalimide is hydrodefluorinated, for example by using sodium hydroxide in the presence of a zinc catalyst, to produce the 3,4,6-trifluoro N-R phthalimide.

An alternative process for producing the phthalimide starting material of this invention also begins with tetrachlorophthalic anhydride. A chlorine is removed first to produce 3,4,6-trichlorophthalic anhydride using, for example, sodium hydroxide in the presence of a zinc catalyst. This is followed by imidization, which produces the trichloro N-R phthalimide, and then fluorination, which produces the 3,4,6-trifluoro-N-R phthalimide. If 3,4,6-trichloro-N-R phthalimide is to be used as the starting material, the fluorination step is omitted. Alternatively, 3,4,6-trichloro-N-R-phthalimide or 3,4,6-tribromo-N-R-phthalimide can be prepared by reacting 3,4,6-trichlorophthalic acid or 3,4,6-tribromo-phthalic acid, respectively, with $RNH_2$.

In the process of this invention, a composition is prepared of the starting phthalimide, water, and a non-oxidizing mineral acid, and the composition is heated to a temperature of about 130° to about 190° C. until the 2,4,5-trihalobenzoic acid is formed. Because the reaction temperature is greater than the boiling point of water, the reaction is conducted under autogenous pressure in an autoclave. While the reaction will proceed at lower temperatures, that requires too much time, and higher temperatures are unnecessary and increase the pressure requirements for the autoclave. The preferred temperature range is about 150° to 170° C.

A mineral acid such as sulfuric acid, hydrochloric acid, nitric acid, or phosphoric acids must be used to prevent the formation of by-product. Hydrofluoric acid is an undesirable mineral acid, however, because it may fluorinate the species to produce by-product. The preferred acid is sulfuric acid because it gives a faster reaction rate. To avoid the formation of by-products, sufficient mineral acid should be used to react stoichiometrically with the amine that is liberated from the imide. For example, while we do not wish to be bound by any theories, we believe that the following reaction occurs with sulfuric acid when the starting material is 3,4,6-trifluoro-N-methylphthalimide:

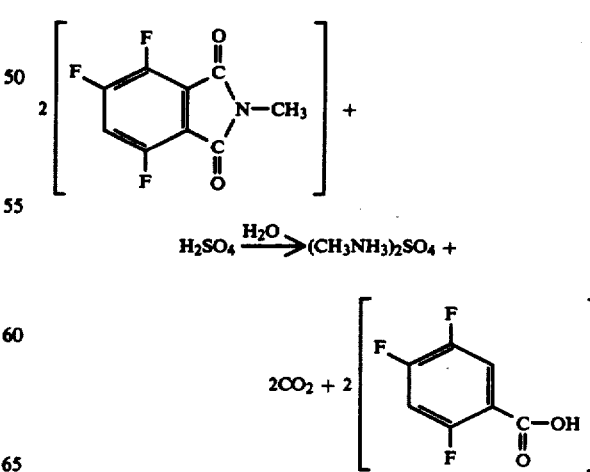

The pressure increase due to formation of $CO_2$ is much less than expected, suggesting that the carbon dioxide liberated may also react with the amine group to form a carbonate salt. The mineral acid can be used in an amount up to about 10 wt% in excess of stoichiometric to minimize by-product formation and to insure a complete reaction. Although the use of even more excess mineral acid may completely eliminate the formation of any amine-induced byproduct, it also tends to slow down the reaction rate.

The starting phthalimide is only partially soluble in water. At least enough water should be used to have a 3:1 wt ratio of water to the starting material to dissolve the starting material, but more than a 10:1 wt ratio is unnecessary. Preferably, the weight ratio of water to starting material is about 6 to 1, as that is enough water to prevent direct heating of the starting material and the resulting formation of tars but is not excessive water.

After the reaction is complete, which typically takes about 1 to about 3 days, the composition is cooled. The product, 2,4,5-trihalobenzoic acid, is extracted from the composition using an organic solvent such as butyl acetate, methyl isobutyl ketone, or ethyl acetate. Ethyl acetate is the preferred extractant because trifluorobenzoic acid has a high solubility in ethyl acetate.

The following examples further illustrate this invention. In the examples, all percentages are by weight.

EXAMPLE 1 (AMOUNT OF SULFURIC ACID USED WAS ADEQUATE)

10 g of 3,4,6-trifluoro-N-methylphthalimide (purity: 89%, about 11% chloro-difluoro-N-methyl phthalimide), was produced by hydrodechlorinating tetrachlorophthalic anhydride in an aqueous NaOH/Zn mixture, imidizing the resulting 3,4,6-trichlorophthalic acid using methylamine, and fluorinating the 3,4,6-trichloro-N-methylphthalimide using KF in sulfolane. The 10 g of imide were charged into a 600 mL autoclave with 300 mL deionized water and 3.2 mL 50% sulfuric acid. The reaction mixture was heated up to 161° C. and the reaction proceeded for about 48 hours while the pressure inside the autoclave increased by about 50 psi. After cooling, the reaction mixture was extracted with ethyl acetate to yield close to 8 g of product containing 80% 2,4,5-trifluoro-benzoic acid, 5.8% 2,3,5-trifluorobenzoic acid and 13% side-product including the 11% impurities derived from chlorodifluoro-N-methyl phthalimide.

EXAMPLE 2 (SLIGHTLY LESS SULFURIC ACID)

10 g of 3,4,6-trifluoro-N-methylphthalimide (92% purity, 8% chlorodifluoro compound), was prepared as in Example 1. The 10 g of imide, 300 mL deionized water, and 2.5 mL 50% sulfuric acid were charged into a 600 mL autoclave. After the reaction mixture was heated up to 156° C. and the reaction had proceeded for about 21 hours, the reaction mixture was analyzed, which showed formation of about 6% side-product containing amine group. After adding 0.5 mL 50% sulfuric acid, the reaction was continued for another 40 hours. About 7.2 g of material wa then recovered by ethyl acetate extraction, which contained about 83% 2,4,5-trifluorobenzoic acid, 8% 2,3,5-trifluorobenzoic acid and 6% side-product containing amine group.

EXAMPLE 3 (NO SULFURIC ACID)

This is a comparative example, outside the scope of this invention.

10 g of 3,4,6-trifluoro-N-methylphthalimide (purity 93%, 7% chlorodifluoro compound), prepared as in Example 1, and 300 mL deionized water were charged into a 600 mL autoclave. The reaction proceeded at 171° C. for about 22 hours and was then cooled down. Extraction of the reaction mixture using ethyl acetate gave 6 g of organic solids containing 68% 2,4,5-trifluorobenzoic acid, 7% 2,3,5-trifluorobenzoic acid, and 25% various side-products.

EXAMPLE 4 (100% EXCESS SULFURIC ACID)

A 19.2 g solid mixture isolated from hydrodefluorination of tetrafluoro-N-methylphthalimide, about 2.7 g 3,4,6-trifluorophthalic acid and a small amount of impurities including the difluoro compound. This mixture was added to 300 mL deionized water with 7.1 g of 98% sulfuric acid. (The acid was roughly twice of the amount required to neutralize amine formed during the reaction). After reacting at 160° C. in an autoclave for about three days, an assay of the material obtained by ethyl acetate extraction of the reaction mixture showed 92% 2,4,5-trifluorobenzoic acid, 4% 2,3,5-trifluorobenzoic acid and less than 4% other dichloro impurities.

EXAMPLE 5 (HCL WAS USED)

9.5 g solid containing about 85% 3,4,6-trifluoro-N-methylphthalimide and 15% 3,4,6-trifluorophthalic acid, was obtained by imidizing tetrachlorophthalic anhydride using methylamine, fluorinating the tetrachloro-N-methylphthalimide using KF in sulfolane, then hydrodefluorinating the tetrafluoro-N-methylphthalimide in aqueous NaOH/Zn mixture. The 9.5 g of solid and 7 g 35.5% HCl were charged into an autoclave with 300 mL deionized water. After the reaction proceeded at 150°-179° C. for 92 hours, an assay of the aqueous solution showed 80% 2,4,5-trifluorobenzoic acid, 5% 2,3,5-trifluorobenzoic acid, 13% 3,4,6-trifluorophthalic acid, and less than 1% 3,4,6-trifluoro-N-methylphthalimide.

EXAMPLE 6 (DIRECT USE OF AQUEOUS LIQUOR FROM HYDRODEFLUORINATION)

300 mL of aqueous liquor was obtained by hydrodefluorinating tetrafluoro-N-methylphthalimide. It contained approximately 17.1 g 3,4,6-trifluoro-N-methylphthalimide and 4.2 g 3,4,6-trifluorophthalic acid in the form of their sodium salts. The liquor was charged into an autoclave with 13 g 98% sulfuric acid. After the reaction proceeded at 160°-164° C. for about 45 hours, an assay showed 78% 2,4,5-trifluorobenzoic acid, 3% 2,3,5-trifluorobenzoic acid, 2% 3,4,6-trifluoro-N-methylphthal-imide/3,4,6-trifluorophthalic acid, and 17% by-product.

EXAMPLE 7 (AMOUNT OF SULFURIC ACID USED WAS INADEQUATE)

As in Example 6, 300 mL aqueous solution containing 29 g solid (about 65% 3,4,6-trifluoro-N-methylphthalimide and 35% 3,4,6-trifluorophthalic acid in their sodium salt form) was charged into an autoclave with 7.3 g 98% sulfuric acid. The reaction was completed at 160° C. in 20.5 hours. Final product assay was 47% 2,4,5-trifluorobenzoic acid, 3% 2,3,5-trifluorobenzoic acid, and 50% by-product. The amount of sulfuric acid used was inadequate because a portion of the sulfuric acid reacted with the residual sodium salts.

We claim:

1. A method of making 2,4,5-trihalobenzoic acid comprising heating to a temperature of about 130° to about 190° C. a composition that comprises (A) a compound having the general formula

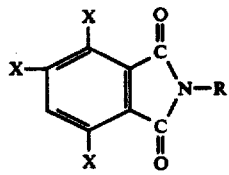

where each "X" is independently selected from fluorine, chlorine, or bromine and "R" is alkyl from $C_1$ to $C_{10}$ or aryl;

(B) water; and (C) a mineral acid.

2. A method according to claim 1 wherein X is fluorine.

3. A method according to claim 2 wherein R is methyl.

4. A method according to claim 1 wherein X is chlorine.

5. A method according to claim 4 wherein R is methyl.

6. A method according to claim 1 wherein X is bromine.

7. A method according to claim 6 wherein R is methyl.

8. A method according to claim 1 wherein said mineral acid is sulfuric acid.

9. A method of making 2,4,5-trihalobenzoic acid comprising (1) heating to a temperature of about 130° to about 190° C. a composition that comprises (A) a compound having the general formula

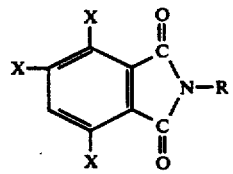

where "X" is fluorine, chlorine, or bromine and "R" is alkyl from $C_1$ to $C_{10}$ or aryl;

(B) water, in a weight ratio to said compound of about 3:1 to about 10:1; and (C) sufficient mineral acid to react with amine formed during said heating;

(2) cooling said composition; and (3) separating said 2,4,5-trihalobenzoic acid from said composition.

10. A method according to claim 9 wherein X is fluorine.

11. A method according to claim 10 wherein R is methyl.

12. A method according to claim 9 wherein X is chlorine.

13. A method according to claim 12 wherein R is methyl.

14. A method according to claim 9 wherein s id mineral acid is sulfuric acid.

15. A method according to claim 9 wherein said weight ratio is about 6:1.

16. A method of making 2,4,5-trifluorobenzoic acid comprising (1) preparing a composition that comprises (A) 3,4,6-trifluoro-N-methyl-phthalimide;

(B) water, in a weight ratio to said 3,4,6-trifluoro-N-methyl phthalimide of about 3:1 to about 10:1; and (C) a stoichiometric amount up to about 10 wt% in excess of stoichiometric of a mineral acid;

(2) heating said composition to a temperature of about 130° to about 190° C;

(3) cooling said composition; and (4) extracting said 2,4,5-trifluorobenzoic acid from said composition using an organic solvent.

17. A method according to claim 16 wherein said mineral acid is sulfuric acid.

18. A method according to claim 16 wherein said organic solvent is ethyl acetate.

19. A method according to claim 16 wherein said weight ratio is about 6:1.

20. A method according to claim 16 wherein said temperature is about 150° to about 170° C.

* * * * *

UNITED STATES PATENT AND TRADEMARK OFFICE
CERTIFICATE OF CORRECTION

PATENT NO. : 5,196,590
DATED : March 23, 1993
INVENTOR(S) : J. Steven Qi, et. al.

It is certified that error appears in the above-indentified patent and that said Letters Patent is hereby corrected as shown below:

On the Title page, item [75], inventor: should read-- J. Steven Qi".--

Signed and Sealed this

Ninth Day of August, 1994

Attest:

BRUCE LEHMAN

Attesting Officer

Commissioner of Patents and Trademarks